(12) United States Patent
Corl

(10) Patent No.: US 8,403,856 B2
(45) Date of Patent: Mar. 26, 2013

(54) ROTATIONAL INTRAVASCULAR ULTRASOUND PROBE WITH AN ACTIVE SPINNING ELEMENT

(75) Inventor: Paul Douglas Corl, Palo Alto, CA (US)

(73) Assignee: Volcano Corporation, San Diego, CA (US)

( * ) Notice: Subject to any disclaimer, the term of this patent is extended or adjusted under 35 U.S.C. 154(b) by 776 days.

(21) Appl. No.: 12/402,278

(22) Filed: Mar. 11, 2009

(65) Prior Publication Data
US 2010/0234736 A1 Sep. 16, 2010

(51) Int. Cl.
*A61B 8/14* (2006.01)
(52) U.S. Cl. ........ 600/462; 600/437; 600/459; 600/466; 606/14; 606/16
(58) Field of Classification Search .................. 600/407, 600/411, 423, 427, 433, 434, 435, 437, 459, 600/466; 606/14, 15, 16
See application file for complete search history.

(56) References Cited

U.S. PATENT DOCUMENTS

| | | | | |
|---|---|---|---|---|
| 4,763,663 A | * | 8/1988 | Uphold et al. | 600/484 |
| 4,803,992 A | * | 2/1989 | Lemelson | 600/342 |
| 5,209,235 A | * | 5/1993 | Brisken et al. | 600/466 |
| 5,313,950 A | * | 5/1994 | Ishikawa et al. | 600/462 |
| 5,485,846 A | | 1/1996 | Webler et al. | |
| 5,827,313 A | * | 10/1998 | Ream | 606/171 |
| 6,017,312 A | * | 1/2000 | Masters | 600/462 |
| 6,758,818 B2 | * | 7/2004 | Pantages et al. | 600/466 |
| 2003/0208119 A1 | * | 11/2003 | Crowley | 600/407 |
| 2006/0173337 A1 | | 8/2006 | Chen et al. | |
| 2006/0173350 A1 | * | 8/2006 | Yuan et al. | 600/466 |
| 2007/0167813 A1 | * | 7/2007 | Lee et al. | 600/459 |
| 2007/0178768 A1 | * | 8/2007 | Harshman et al. | 439/660 |
| 2008/0161696 A1 | | 7/2008 | Schmitt et al. | |
| 2008/0177183 A1 | * | 7/2008 | Courtney et al. | 600/463 |
| 2009/0221958 A1 | * | 9/2009 | Beyar et al. | 604/95.01 |

OTHER PUBLICATIONS

Korean Intellectual Property Office "Notification of Transmittal of the International Search Report and The Written Opinion of the International Searching Authority, or the Declaration" for PCT/US2010/026491, mailed Sep. 28, 2010, 8 pages.

* cited by examiner

*Primary Examiner* — James Kish
*Assistant Examiner* — Michael N Fisher
(74) *Attorney, Agent, or Firm* — Haynes and Boone, LLP

(57) ABSTRACT

An intravascular ultrasound probe is disclosed, incorporating features for utilizing an advanced transducer technology on a rotating transducer shaft. In particular, the probe accommodates the transmission of the multitude of signals across the boundary between the rotary and stationary components of the probe required to support an advanced transducer technology. These advanced transducer technologies offer the potential for increased bandwidth, improved beam profiles, better signal to noise ratio, reduced manufacturing costs, advanced tissue characterization algorithms, and other desirable features. Furthermore, the inclusion of electronic components on the spinning side of the probe can be highly advantageous in terms of preserving maximum signal to noise ratio and signal fidelity, along with other performance benefits.

20 Claims, 6 Drawing Sheets

ROTATIONAL INTRAVASCULAR ULTRASOUND PROBE WITH AN ACTIVE SPINNING ELEMENT

BACKGROUND

Intravascular Ultrasound (IVUS) has become an important interventional diagnostic procedure for imaging atherosclerosis and other vessel diseases and defects. In the procedure, an IVUS catheter is threaded over a guidewire into a blood vessel of interest, and images are acquired of the atherosclerotic plaque and surrounding area using ultrasonic echoes. This information is much more descriptive than the traditional standard of angiography, which shows only a two-dimensional shadow of the vessel lumen. Some of the key applications of IVUS include: determining a correct diameter and length of a stent to choose for dilating an arterial stenosis, verifying that a post-stenting diameter and luminal cross-section area are adequate, verifying that a stent is well apposed against a vessel wall to minimize thrombosis and optimize drug delivery (in the case of a drug eluting stent) and identifying an exact location of side-branch vessels. In addition, new techniques such as virtual histology (RF signal-based tissue characterization) show promise of aiding identification of vulnerable plaque (i.e., plaque which is prone to rupture and lead to onset of a heart attack).

There are two types of IVUS catheters commonly in use: mechanical/rotational IVUS catheters and solid state catheters. In a rotational IVUS catheter, a single transducer consisting of a piezoelectric crystal is rotated at approximately 1800 revolutions per minute while the element is intermittently excited with an electrical pulse. This excitation causes the element to vibrate at a frequency dependent upon the particulars of the transducer design. Depending on the dimensions and characteristics of the transducer, this operating frequency is typically in the range of 8 to 50 MHz. In general terms, a higher frequency of operation provides better resolution and a smaller catheter, but at the expense of reduced depth of penetration and increased echoes from the blood (making the image more difficult to interpret). A lower frequency of operation is more suitable for IVUS imaging in larger vessels or within the chambers of the heart.

The rotational IVUS catheter has a drive shaft disposed within the catheter body. The transducer is attached to the distal end of the drive shaft. The typical single element piezoelectric transducer requires only two electrical leads, with this pair of leads serving two separate purposes: (1) delivering the intermittent electrical transmit pulses to the transducer, and (2) delivering the received electrical echo signals from the transducer to the receiver amplifier (during the intervals between transmit pulses). The IVUS catheter is removably coupled to an interface module, which controls the rotation of the drive shaft within the catheter body and contains the transmitter and receiver circuitry for the transducer. Because the transducer is on a rotating drive shaft and the transmitter and receiver circuitry is stationary, a device must be utilized to carry the transmit pulse and received echo across a rotating interface. This can be accomplished via a rotary transformer, which comprises two halves, separated by a narrow air gap that permits electrical coupling between the primary and secondary windings of the transformer while allowing relative motion (rotation) between the two halves. The spinning element (transducer, electrical leads, and driveshaft) is attached to the spinning portion of the rotary transformer, while the stationary transmitter and receiver circuitry contained in the interface module are attached to the stationary portion of the rotary transformer.

The other type of IVUS catheter is a solid state (or phased array) catheter. This catheter has no rotating parts, but instead includes an array of transducer elements (for example 64 elements), arrayed in a cylinder around the circumference of the catheter body. The individual elements are fired in a specific sequence under the control of several small integrated circuits mounted in the tip of the catheter, adjacent to the transducer array. The sequence of transmit pulses interspersed with receipt of the echo signals provides the ultrasound data required to reconstruct a complete cross-sectional image of the vessel, similar in nature to that provided by a rotational IVUS device.

Currently, most IVUS systems rely on conventional piezoelectric transducers, built from piezoelectric ceramic (commonly referred to as the crystal) and covered by one or more matching layers (typically thin layers of epoxy composites or polymers). Two advanced transducer technologies that have shown promise for replacing conventional piezoelectric devices are the PMUT (Piezoelectric Micromachined Ultrasonic Transducer) and CMUT (Capacitive Micromachined Ultrasonic Transducer). PMUT and CMUT transducers may provide improved image quality over that provided by the conventional piezoelectric transducer, but these technologies have not been adopted for rotational IVUS applications due to the larger number of electrical leads they require, among other factors.

There are many potential advantages of these advanced transducer technologies, some of which are enumerated here. Both PMUT and CMUT technologies promise reduced manufacturing costs by virtue of the fact that these transducers are built using wafer fabrication techniques to mass produce thousands of devices on a single silicon wafer. This is an important factor for a disposable medical device such as an IVUS catheter. These advanced transducer technologies provide broad bandwidth (>100%) in many cases compared to the 30-50% bandwidth available from the typical piezoelectric transducer. This broader bandwidth translates into improved depth resolution in the IVUS image, and it may also facilitate multi-frequency operation or harmonic imaging, either of which can help to improve image quality and/or enable improved algorithms for tissue characterization, blood speckle reduction, and border detection. Advanced transducer technologies also offer the potential for improved beam characteristics, either by providing a focused transducer aperture (instead of the planar, unfocused aperture commonly used), or by implementing dynamically variable focus with an array of transducer elements (in place of the traditional single transducer element).

BRIEF SUMMARY

The present invention provides the enabling technology allowing advanced transducer technology to be introduced into a rotational IVUS catheter. This in turn will provide improved image quality and support advanced signal processing to facilitate more accurate diagnosis of the medical condition within the vessel. All of this can be achieved in a cost-effective way, possibly at a lower cost than the conventional technology.

Embodiments of an intravascular ultrasound probe are disclosed herein. The probe has features for utilizing an advanced transducer technology on a rotating transducer shaft. In particular, the probe accommodates the transmission of the multitude of signals across the boundary between the rotary and stationary components of the probe required to support an advanced transducer technology. These advanced transducer technologies offer the potential for increased bandwidth, improved beam profiles, better signal to noise ratio, reduced manufacturing costs, advanced tissue characterization algorithms, and other desirable features. Furthermore, the inclusion of electronic components on the spinning side of the probe can be highly advantageous in terms of preserving maximum signal to noise ratio and signal fidelity, along with other performance benefits.

In a disclosed embodiment, a rotational intravascular ultrasound probe for insertion into a vasculature is described. The rotational intravascular ultrasound probe can comprise an elongate catheter, an elongate transducer shaft, a spinning element, and a motor. The elongate catheter can have a flexible body. The elongate transducer shaft can be disposed within the flexible body and can have a drive cable and a transducer coupled to the drive cable. The spinning element can be coupled to the transducer shaft and can have an electronic component coupled thereto that is in electrical contact with the transducer. A motor may be coupled to the spinning element for rotating the spinning element and the transducer shaft.

In another disclosed embodiment, an interface module for a rotational intravascular ultrasound probe for insertion into a vasculature is described. The interface module can comprise a connector, a spinning element, and a motor. The connector can be used for attachment to a catheter having a transducer shaft with a transducer. The spinning element can be coupled to the connector and can have an electronic component coupled thereto that is in electrical contact with the connector. A motor may be coupled to the spinning element for rotating the spinning element.

In yet another disclosed embodiment, an interface module for a rotational intravascular ultrasound probe for insertion into a vasculature is described. The interface module can comprise a printed circuit board, a connector, a spinning element, and a motor. The connector can be used for attachment to a catheter having a transducer shaft with a transducer. The spinning element can be coupled to the connector. The spinning element has more than two signal pathways electrically connecting the spinning element to the connector. A motor may be coupled to the spinning element for rotating the spinning element.

DETAILED DESCRIPTION

Turning to the figures, representative illustrations of rotational intravascular ultrasound (IVUS) probes, some of which include active spinning elements, are shown therein. An active spinning element can increase the number of signal paths available for the operation of the transducer so that advanced transducer technologies, such as PMUT (Piezoelectric Micromachined Ultrasonic Transducer) and CMUT (Capacitive Micromachined Ultrasonic Transducer), can be utilized with a rotational IVUS probe. In addition, an active spinning element can include active electronics on the rotary side of the probe.

Figure 1:
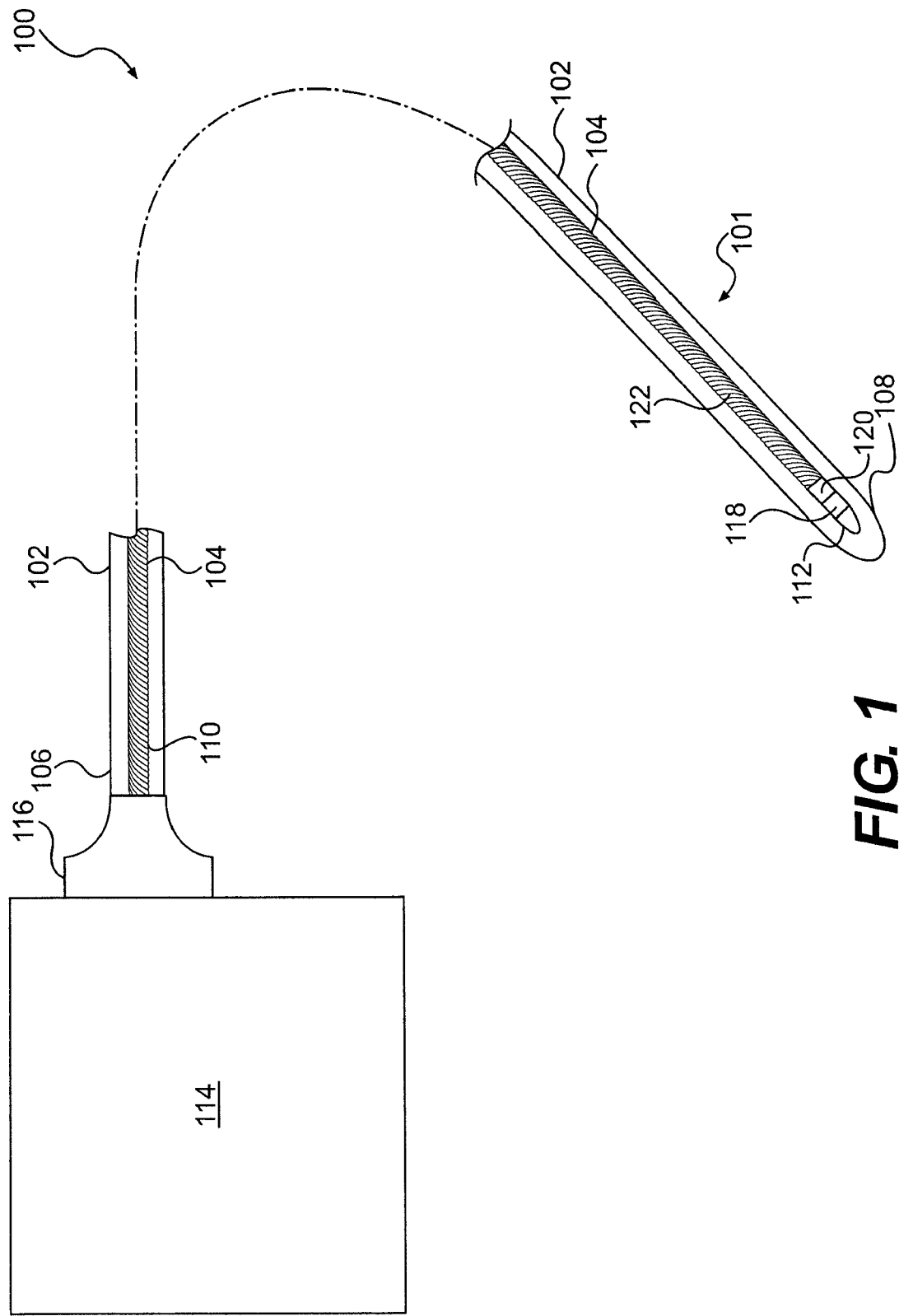
FIG. 1 is a simplified fragmentary diagrammatic view of a rotational IVUS probe.

Referring specifically to FIG. 1, a rotational intravascular ultrasound probe 100 for insertion into a patient for diagnostic imaging is shown. The probe 100 comprises a catheter 101 having a catheter body 102 and a transducer shaft 104. The catheter body 102 is flexible and has both a proximal end portion 106 and a distal end portion 108. The catheter body 102 is a sheath surrounding the transducer shaft 104. For explanatory purposes, the catheter body 102 in FIG. 1 is illustrated as visually transparent such that the transducer shaft 104 disposed therein can be seen, although it will be appreciated that the catheter body 102 may or may not be visually transparent. The transducer shaft 104 is flushed with a sterile fluid, such as saline, within the catheter body 102. The fluid serves to eliminate the presence of air pockets around the transducer shaft 104 that adversely affect image quality. The fluid can also act as a lubricant. The transducer shaft 104 has a proximal end portion 110 disposed within the proximal end portion 106 of the catheter body 102 and a distal end portion 112 disposed within the distal end portion 108 of the catheter body 102.

The distal end portion 108 of the catheter body 102 and the distal end portion 112 of the transducer shaft 104 are inserted into a patient during the operation of the probe 100. The usable length of the probe 100 (the portion that can be inserted into a patient) can be any suitable length and can be varied depending upon the application. The distal end portion 112 of the transducer shaft 104 includes a transducer subassembly 118.

The proximal end portion 106 of the catheter body 102 and the proximal end portion 110 of the transducer shaft 104 are connected to an interface module 114 (sometimes referred to as a patient interface module or PIM). The proximal end portions 106, 110 are fitted with a catheter hub 116 that is removably connected to the interface module 114.

The rotation of the transducer shaft 104 within the catheter body 102 is controlled by the interface module 114, which provides a plurality of user interface controls that can be manipulated by a user. The interface module 114 also communicates with the transducer subassembly 118 by sending and receiving electrical signals to and from the transducer subassembly 118 via wires within the transducer shaft 104. The interface module 114 can receive, analyze, and/or display information received through the transducer shaft 104. It will be appreciated that any suitable functionality, controls, information processing and analysis, and display can be incorporated into the interface module 114.

The transducer shaft 104 includes a transducer subassembly 118, a transducer housing 120, and a drive cable 122. The transducer subassembly 118 is coupled to the transducer housing 120. The transducer housing 120 is attached to the drive cable 122 at the distal end portion 112 of the transducer shaft 104. The drive cable 122 is rotated within the catheter body 102 via the interface module 114 to rotate the transducer housing 120 and the transducer subassembly 118. The transducer subassembly 118 can be of any suitable type, including but not limited to one or more advanced transducer technologies such as PMUT or CMUT. The transducer subassembly 118 can include either a single transducer or an array.

Figure 2:
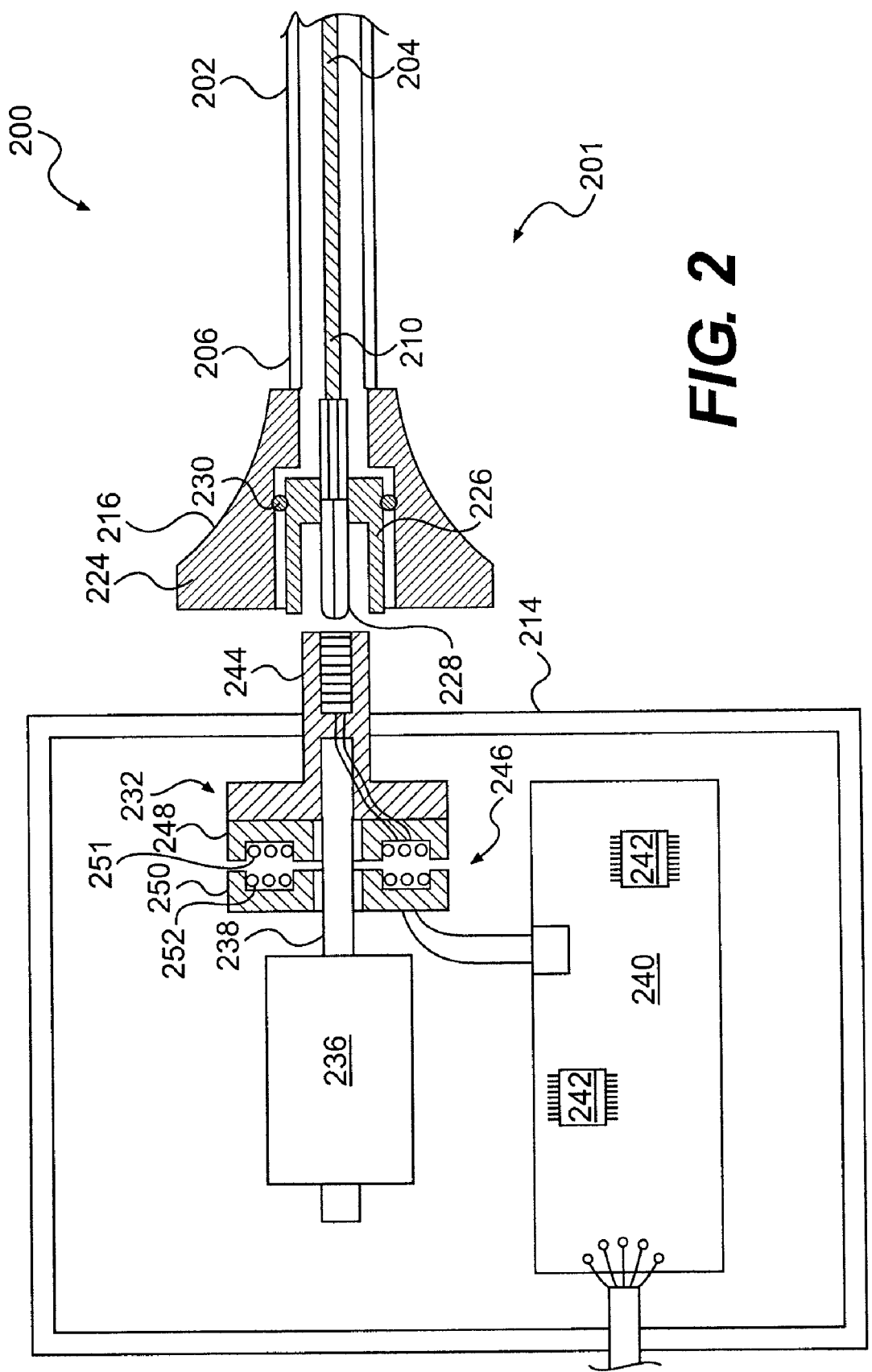
FIG. 2 is a simplified fragmentary diagrammatic view of an interface module and catheter for the rotational IVUS probe of FIG. 1 incorporating basic ultrasound transducer technology.

FIG. 2 shows a rotational IVUS probe 200 utilizing a common spinning element 232. The probe 200 has a catheter 201 with a catheter body 202 and a transducer shaft 204. As shown, the catheter hub 216 is near the proximal end portion 206 of the catheter body 202 and the proximal end portion 210 of the transducer shaft 204. The catheter hub 216 includes a stationary hub housing 224, a dog 226, a connector 228, and bearings 230. The dog 226 mates with a spinning element 232 for alignment of the hub 216 with the interface module 214 and torque transmission to the transducer shaft 204. The dog 226 rotates within the hub housing 224 utilizing the bearings 230. The connector 228 in this figure is coaxial. The connector 228 rotates with the spinning element 232, described further herein.

As shown, the interior of the interface module 214 includes a motor 236, a motor shaft 238, a printed circuit board (PCB) 240, the spinning element 232, and any other suitable components for the operation of the IVUS probe 200. The motor 236 is connected to the motor shaft 238 to rotate the spinning element 232. The printed circuit board 240 can have any suitable number and type of electronic components 242, including but not limited to the transmitter and the receiver for the transducer.

The spinning element 232 has a complimentary connector 244 for mating with the connector 228 on the catheter hub 216. As shown, the spinning element 232 is coupled to a rotary portion 248 of a rotary transformer 246. The rotary portion 248 of the transformer 246 passes the signals to and from a stationary portion 250 of the transformer 246. The stationary portion 250 of the transformer 246 is wired to the transmitter and receiver circuitry on the printed circuit board 240.

The transformer includes an insulating wire that is layered into an annular groove to form a two- or three-turn winding. Each of the rotary portion 250 and the stationary portion 248 has a set of windings, such as 251 and 252 respectively. Transformer performance can be improved through both minimizing the gap between the stationary portion 250 and the rotary portion 248 of the transformer 246 and also by placing the windings 251, 252 as close as possible to each other.

Advanced transducer technologies can require more than the two conductive signal lines that a single piezoelectric transducer utilizes on a conventional rotational IVUS probe. For example, in addition to signal pathways for ultrasound information communicated with the transducer, certain advanced transducer technologies also require a power supply in order to operate. In order to pass the necessary multiple of signals between the advanced transducer technology and the interface module, a suitable structure may be needed to transmit ultrasound signals, power, and any other suitable signals across the boundary between the rotating and stationary mechanical components. Particularly for ultrasound signals, the mode of transmission must also maintain reliable signal quality, without excess noise, sufficient for the interface module to form a reliable image of the target tissue from the sensitive ultrasound signals. It will be appreciated that any suitable signals can be communicated across the boundary between the rotating and stationary mechanical components including, but not limited to, A-scan RF data, power transmit pulses, low amplitude receive signals, DC power and/or bias, AC power, and/or various control signals. The signal transfer across the boundary between the rotating and stationary mechanical components can have high frequency capability and broadband response.

Multiple signal transfer pathways are presented herein for communicating signals across the boundary of the rotating and stationary parts. Each of these pathways are explained in further detail herein, and for purposes of discussion and explanation, certain pathways may be shown in combination with one another. It will be appreciated, however, that any of these pathways may be utilized in any suitable combination with one another to permit any suitable number of total signal pathways. Furthermore, as will be explained in further detail below, certain signal transfer pathways can be more conducive to transmitting either power or other signals, such as ultrasound signals.

Figure 3:
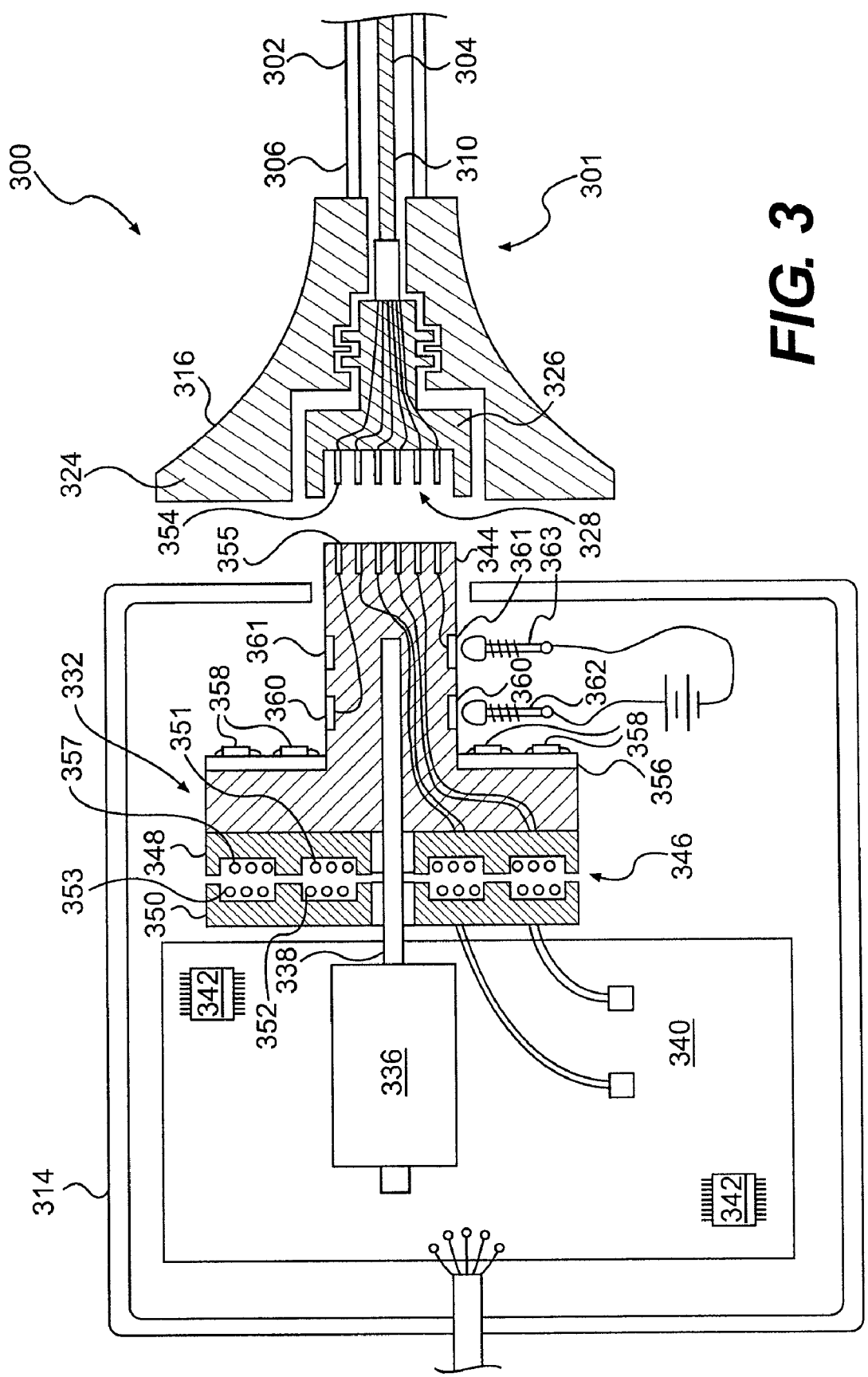
FIG. 3 is a simplified fragmentary diagrammatic view of an embodiment of an interface module and catheter for the rotational IVUS probe of FIG. 1 incorporating an advanced ultrasound transducer technology.

Referring to FIG. 3, an embodiment of a rotational IVUS probe 300 having an interface module 314 and catheter 301 suitable for use with an advanced transducer technology is represented. As shown, the probe 300 has a catheter body 302, a transducer shaft 304, and a catheter hub 316. The catheter body 302 has a proximal end 306 and the transducer shaft 304 has a proximal end 310. The catheter hub 316 includes a stationary exterior housing 324, a dog 326, and a connector 328. The connector 328 is represented with six conductive lines 354 shown in this embodiment. It will be appreciated, however, that any suitable number of conductive lines can be utilized.

As shown, the interior of the interface module 314 can include a motor 336, a motor shaft 338, a main printed circuit board (PCB) 340, a spinning element 332, and any other suitable components for the operation of the IVUS probe 300. The motor 336 is connected to the motor shaft 338 to rotate the spinning element 332. The printed circuit board 340 can have any suitable number and type of electronic components 342.

The spinning element 332 has a complimentary connector 344 for mating with the connector 328 on the catheter hub 316. The connector 344 can have conductive lines, such as 355, that contact the conductive lines, such as 354, on the connector 328. As shown, the spinning element 332 is coupled to a rotary portion 348 of a rotary transformer 346. The rotary portion 348 of the transformer 346 passes the signals to and from a stationary portion 350 of the transformer 346. The stationary portion 350 of the transformer 346 is electrically connected to the printed circuit board 340.

In this embodiment, the transformer 346 has multiple sets of windings for transmitting multiple signals across the transformer 346. Specifically, as shown, the rotary portion 348 and the stationary portion 350 of the transformer 346 each have two sets of windings, such as windings 352, 353 on the stationary portion 350 and windings 351, 357 on the rotary portion 348, to transmit two signals across the transformer 346. In this way, more signal pathways are available for a probe 300 utilizing an advanced transducer technology. It will be appreciated that any suitable number of windings may be used to transmit any suitable number of signals across the transformer 346. In alternative embodiments, planar flex circuits can be used in place of the windings in the transformer. The planar flex circuits can be placed very close to one another to enhance signal quality.

Another consideration for advanced transducer technologies is that the probe 300 can benefit from the utilization of certain active electronic components and circuitry in order to facilitate and/or complement the operation of the transducer. Through active electronic components and circuitry on the spinning element 332, more complex electrical communication can take place between the interface module 314 and the transducer. Furthermore, by handling certain signal processing functions on the spinning element 332, the number of signals that need to pass across the spinning element 332 can, in some embodiments, be reduced.

As shown, a printed circuit board 356 can be coupled to the spinning element 332. The printed circuit board 356 can have any suitable number of electronic components 358 coupled thereto. Any suitable number of printed circuit boards 356 having any suitable number and type of electronic components 358 can be utilized on the spinning element 332. The electronic components on the spinning element 332 allow for signal processing to take place on the spinning side of the probe 300 before the signal is communicated across the rotary/stationary boundary.

Typically, advanced transducer technologies require a DC power source. To provide DC power to the transducer, the spinning element 332 can be fitted with contacts, such as slip ring contacts 360, 361, which are respectively engaged by stationary brushes 362, 363 within the interface module 314. Each of the slip rings 360, 361 is coupled to a respective conductive line, such as 355, in the connector 344.

In other embodiments, the transducer can be powered by an AC power source. For example, instead of using brushes and contacts, AC power can be transmitted through a set of windings in the transformer 346. Once the power has passed across from the stationary portion 350 of the transformer 346 to the rotary portion 348 of the transformer 346, it can be passed to a power supply circuit, such as a diode rectifier, on the spinning element 332 that rectifies the AC power into DC power. The rectifier can be coupled to the printed circuit board 356 on the spinning element 332 as one of the electronic components 358. After the AC power is converted to DC power, the DC power can be used to power the transducer, as well as the other electronic components 358 included on printed circuit board 356.

Figure 4:
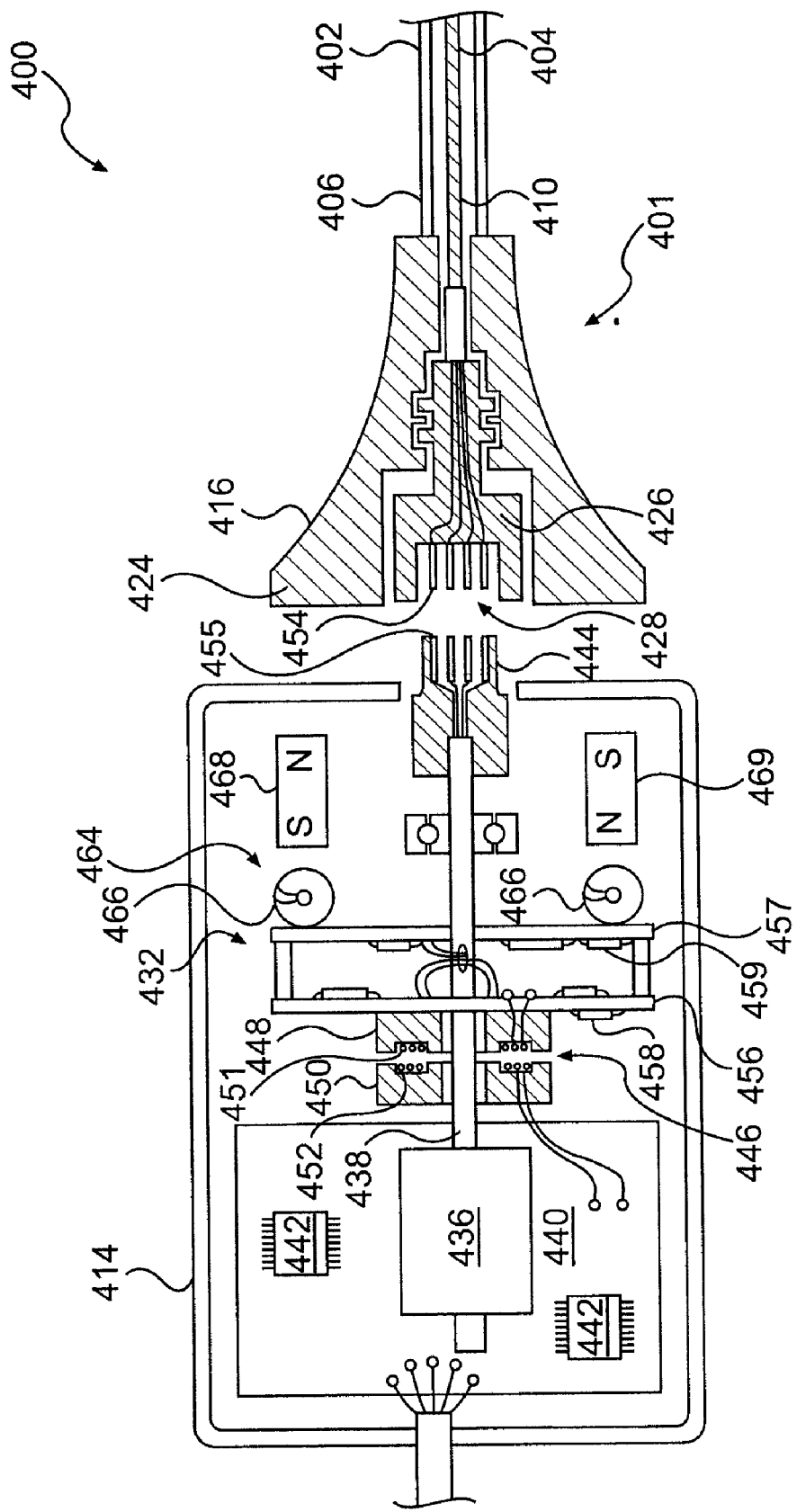
FIG. 4 is a simplified fragmentary diagrammatic view of another embodiment of an interface module and catheter for the rotational IVUS probe of FIG. 1 incorporating an advanced ultrasound transducer technology.

Turning to FIG. 4, an embodiment of a rotational IVUS probe 400 having an interface module 414 and catheter 401 suitable for use with an advanced transducer technology is represented. As shown, the probe 400 has a catheter body 402, a transducer shaft 404, and a catheter hub 416. The catheter body 402 has a proximal end portion 406, and the transducer shaft 404 has a proximal end portion 410. The catheter hub 416 includes a stationary exterior housing 424, a dog 426, and a connector 428. The connector 428 is represented with four conductive lines 454 shown in this embodiment. It will be appreciated, however, that any suitable number of conductive lines can be utilized.

As shown, the interior of the interface module 414 can include a motor 436, a motor shaft 438, a main printed circuit board (PCB) 440, a spinning element 432, and any other suitable components for the operation of the IVUS probe 400. The motor 436 is connected to the motor shaft 438 to rotate the spinning element 432. The printed circuit board 440 can have any suitable number and type of electronic components 442.

The spinning element 432 has a complimentary connector 444 for mating with the connector 428 on the catheter hub 416. The connector 444 can have conductive lines, such as 455, that contact the conductive lines, such as 454, on the connector 428. As shown, the spinning element 432 is coupled to a rotary portion 448 of a rotary transformer 446. The rotary portion 448 of the transformer 446 passes the signals to and from a stationary portion 450 of the transformer. The stationary portion 450 of the transformer 446 is electrically connected to the printed circuit board 440.

As shown, the rotary portion 448 and the stationary portion 450 of the transformer 446 each have a set of windings 451, 452 to transmit a signal across the transformer 446. It will be appreciated that any suitable number of windings may be used to transmit any suitable number of signals across the transformer 446. In this embodiment, the transformer 446 can be used to transfer the ultrasound signal. It will also be appreciated that a planar flex circuit may be used in place of one or more of the sets of windings as previously described.

The probe 400 can benefit from the utilization of certain electronic components and circuitry in order to facilitate and/or complement the operation of the transducer. As shown, one or more printed circuit boards 456, 457 can be coupled to the spinning element 432. The printed circuit boards 456, 457 can have any suitable number of electronic components, such as 458 and 459, coupled thereto. It will be appreciated that any suitable number of printed circuit boards 456, 457 having any suitable number and type of electronic components 458, 459 can be utilized on the spinning element 432. Electronic components on the spinning element 432 allow for signal processing to take place on the spinning side of the probe 400 before the signal is communicated across the rotary/stationary boundary.

In this embodiment, power is provided to the transducer using a generator mechanism 464 to generate power locally. As illustrated in the figure, the generator mechanism 464 includes a generator coil 466 and a plurality of stator magnets 468, 469. The generator coil 466 can be attached to the spinning element 432 to rotate with the spinning element 432 and generate power. The power generated is AC power, so a power supply circuit, such as a diode rectifier, can be used to convert the AC power into DC power. The rectifier can be coupled to the printed circuit boards 456, 457 on the spinning element 432. After rectification, the DC power can be used to power the transducer as well as the other electronic components 458, 459 included on the printed circuit boards 456, 457. It will be appreciated that any suitable generator can be utilized to provide power to the transducer.

Figure 5:
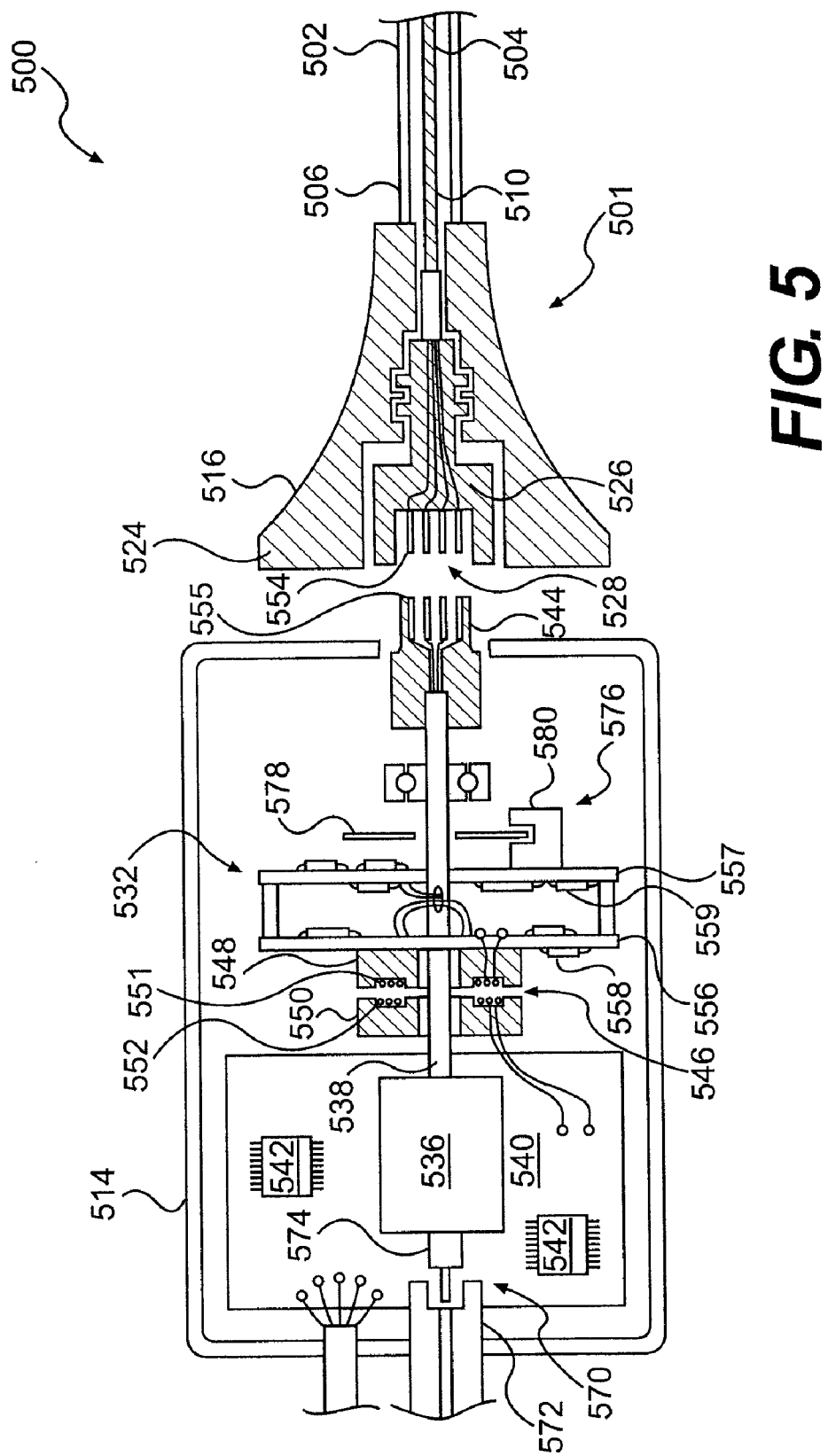
FIG. 5 is a simplified fragmentary diagrammatic view of another embodiment of an interface module and catheter for the rotational IVUS probe of FIG. 1 incorporating an advanced ultrasound transducer technology.

Another embodiment of a rotational IVUS probe 500 having an interface module 514 and catheter 501 suitable for use with an advanced transducer technology is represented in FIG. 5. As shown, the probe has a catheter body 502, a transducer shaft 504, and a catheter hub 516. The catheter body 502 has a proximal end portion 506, and the transducer shaft 504 has a proximal end portion 510. The catheter hub 516 includes a stationary exterior housing 524, a dog 526, and a connector 528. The connector 528 is represented with four conductive lines 554 shown in this embodiment. It will be appreciated, however, that any suitable number of conductive lines can be utilized.

As shown, the interior of the interface module 514 can include a motor 536, a motor shaft 538, a main printed circuit board (PCB) 540, a spinning element 532, and any other suitable components for the operation of the IVUS probe 500. The motor 536 is connected to the motor shaft 538 to rotate the spinning element 532. The printed circuit board 540 can have any suitable number and type of electronic components 542.

The spinning element 532 has a complimentary connector 544 for mating with the connector on the catheter hub 516. The connector 544 can have conductive lines, such as 555, that contact the conductive lines, such as 554, on the connector 528. As shown, the spinning element 532 is coupled to a rotary portion 548 of a rotary transformer 546. The rotary portion 548 of the transformer 546 passes the signals to and from the stationary portion 550 of the transformer 546. The stationary portion 550 of the transformer 546 is electrically connected to the printed circuit board 540.

As shown, the rotary portion 548 and the stationary portion 550 of the transformer 546 each have one set of windings 551, 552 to transmit a signal across the transformer 546. It will be appreciated that any suitable number of windings 551, 552 may be used to transmit any suitable number of signals across the transformer 546. In this embodiment, the transformer 546 is used to transfer AC power. Once the power has passed across from the stationary portion 550 of the transformer 546 to the rotary portion 548 of the transformer 546, it can be passed to a power supply circuit, such as a diode rectifier, on the spinning element 532 that rectifies the AC power into DC power. The rectifier can be coupled to the printed circuit boards 556, 557 on the spinning element 532. After the AC power is converted to DC power, the DC power can be used to power the transducer as well as the other electronic components 558, 559 included on the printed circuit boards 556, 557. It will also be appreciated that a planar flex circuit may be used in place of one or more of the sets of windings as previously described.

As previously mentioned, the probe 500 can benefit from the utilization of certain electronic components and circuitry in order to facilitate and/or complement the operation of the transducer. As shown, one or more printed circuit boards 556, 557 can be coupled to the spinning element 532. The printed circuit boards 556, 557 can have any suitable number of electronic components, such as 558 and 559, coupled thereto. It will be appreciated that any suitable number of printed circuit boards 556, 557 having any suitable number and type of electronic components 558, 559 can be utilized on the spinning element 532. Electronic components 558, 559 on the spinning element 532 allow for signal processing to take place on the spinning side of the probe 500 before the signal is communicated across the rotary/stationary boundary.

In this embodiment, an optical coupler 570 is used to transmit the ultrasound signal. It will be appreciated that any suitable optical coupler may be used. The optical coupler can have a first end 572 and a second end 574. The first end 572 can be stationary and receive optical signals from the second end 574, which can be coupled directly or indirectly to the spinning element 532. The ultrasound signal can be transmitted to circuitry on the printed circuit board 540 or can be carried external to the interface module 514.

One illustrative example of how the ultrasound signal could be communicated over this optical path is that the printed circuit boards 556, 557 could include a high speed analog to digital converter (ADC) among electronic components 558, 559. This ADC would be used to digitize the ultrasound echo signal and convert the resultant digital data into a serial bit stream. This serial data would then be provided to an optical transmitter, such as a laser diode circuit, also included on printed circuit boards 558, 559 to transmit the high-speed serial bit stream over the rotating optical coupler 570 to an optical receiver circuit included on printed circuit board 540 or located remotely from the interface module 514.

As shown, a structure may be provided that can provide feedback as to the angular position of the transducer. For example, an optical device 576 may be provided that includes a stationary encoder wheel 578 and an optical detector 580. The optical detector 580 can be attached to a printed circuit board 557 on the spinning element 532.

Figure 6:
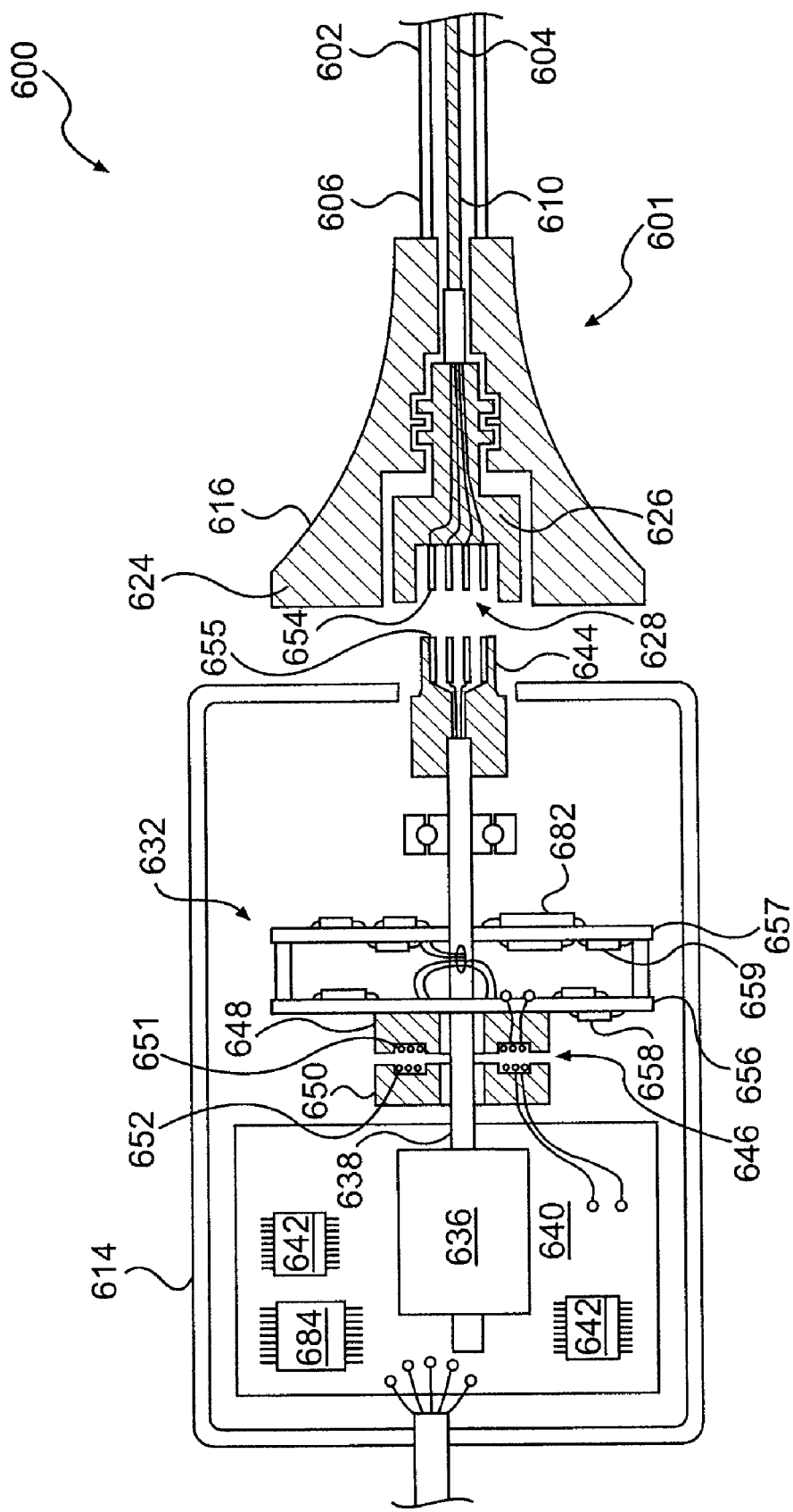
FIG. 6 is a simplified fragmentary diagrammatic view of another embodiment of an interface module and catheter for the rotational IVUS probe of FIG. 1 incorporating an advanced ultrasound transducer technology.

Another embodiment of a rotational IVUS probe 600 having an interface module 614 and catheter 601 suitable for use with an advanced transducer technology is represented in FIG. 6. As shown, the probe 600 has a catheter body 602, a transducer shaft 604, and a catheter hub 616. The catheter body 602 has a proximal end portion 606, and the transducer shaft 604 has a proximal end portion 610. The catheter hub 616 includes a stationary exterior housing 624, a dog 626, and a connector 628. The connector is represented with four conductive lines, such as 654, shown in this embodiment. It will be appreciated, however, that any suitable number of conductive lines 654 can be utilized.

As shown, the interior of the interface module 614 can include a motor 636, a motor shaft 638, a main printed circuit board (PCB) 640, a spinning element 632, and any other suitable components for the operation of the IVUS probe 600. The motor 636 is connected to the motor shaft 638 to rotate the spinning element 632. The main printed circuit board 640 can have any suitable number and type of electronic components 642 including but not limited to the transmitter and the receiver for the transducer.

The spinning element 632 has a complimentary connector 644 for mating with the connector 628 on the catheter hub 616. The connector 644 can have conductive lines, such as 655, that contact the conductive lines, such as 654, on the connector 628. As shown, the spinning element 632 is coupled to a rotary portion 648 of a rotary transformer 646. The rotary portion 648 of the transformer 646 passes the signals to and from the stationary portion 650 of the transformer 646. The stationary portion 650 of the transformer 646 is electrically connected to the printed circuit board 640.

As shown, the rotary portion 648 and the stationary portion 650 of the transformer 646 each have a set of windings 651, 652 to transmit a signal across the transformer 646. It will be appreciated that any suitable number of windings may be used to transmit any suitable number of signals across the transformer 646. In this embodiment, the transformer 646 is used to transfer AC power. Once the power has passed across from the stationary portion 650 of the transformer 646 to the rotary portion 648 of the transformer 646, it can be passed to a power supply circuit, such as a diode rectifier, on the spinning element 632 that rectifies the AC power into DC power. The rectifier can be coupled to printed circuit boards 656, 657 on the spinning element 632. After the AC power is converted to DC power, the DC power can be used to power the transducer as well as the other electronic components 658, 659 included on the printed circuit boards 656, 657. It will also be appreciated that a planar flex circuit may be used in place of one or more of the sets of windings as previously described.

As previously mentioned, the probe can benefit from the utilization of certain electronic components and circuitry in order to facilitate and/or complement the operation of the transducer. As shown, one or more printed circuit boards 656, 657 can be coupled to the spinning element 632. The printed circuit boards 656, 657 can have any suitable number of electronic components, such as 658 and 659, coupled thereto. It will be appreciated that any suitable number of printed circuit boards 656, 657 having any suitable number and type of electronic components 658, 659 can be utilized on the spinning element 632. Electronic components 658, 659 on the spinning element 632 allow for signal processing to take place on the spinning side of the probe 600 before the signal is communicated across the rotary/stationary boundary.

In this embodiment, a wireless communication mechanism is used to transmit the ultrasound signal. Any suitable wireless communication mechanism may be used including, but not limited to, wireless mechanisms utilizing radio frequency or infrared. As shown, the wireless communication mechanism includes transmitter and/or receiver components 682 and 684. The transmitter and/or receiver component 682 can be attached to any suitable location such as the printed circuit board 657 on the spinning element 632. The transmitter and/or receiver component 684 can likewise be placed in any suitable location including the main printed circuit board 640 in the interface module 614.

Therefore, it will be appreciated that signals can be carried across the rotating and stationary mechanical components via any suitable mechanism including, but not limited to, a transformer, an optical coupler, a wireless communication mechanism, a generator, and/or brushes/contacts. In certain embodiments, a transformer, an optical coupler, and/or a wireless communication mechanism can be utilized to carry signals such as an ultrasound signal. In certain embodiments, a transformer, a power generator, and/or brushes/contacts can be utilized to convey power to the transducer.

Furthermore, the spinning element can have one or more printed circuit boards with a suitable number and type of active electronic components and circuitry, thus making the spinning element an active spinning element. Examples of electronic components that can be utilized with the active spinning element include, but are not limited to, power supply circuits (such as a generator, rectifier, regulator, high voltage step-up converter, etc.), transmitters (including tripolar transmitters), time-gain-control (TGC) amplifiers, amplitude and/or phase detectors, ADC converters, optical transceivers, encoder circuits, wireless communication components, microcontrollers, and any other suitable components. In addition, the spinning element can include encoder and timing logic such that it can internally generate the transmit triggers, and thus, eliminate the need to communicate a timing signal across the spinning element. Through the embodiments described herein, excellent image quality is possible including wide bandwidth, frequency-agility, low ringdown, focused beam (including dynamically focused beam), and harmonic capability.

As mentioned, any suitable advanced transducer technology may be used, including but not limited to PMUT and CMUT transducers, either as single transducers or arrays. As an example, a PMUT transducer can be formed by depositing a piezoelectric polymer (such as polyvinylidene fluoride—PVDF) onto a micromachined silicon substrate. The silicon substrate can include an amplifier and protection circuit to buffer the signal from the PVDF transducer. It can be important to include the amplifier immediately adjacent to the PVDF element because the capacitance of the electrical cables can dampen the signal from the high impedance PVDF transducer. The amplifier typically requires DC power, transmit input(s), and amplifier output connections. The PVDF transducer can be a focused transducer to provide excellent resolution.

As mentioned above, having an active spinning element, such as is described herein, permits the utilization of an advanced transducer technology on a rotational IVUS probe. In addition, having an active spinning element can facilitate certain advanced operations of the probe. The enhanced bandwidth of the probe utilizing the active spinner permits the probe to obtain information at a plurality of different frequencies. By way of example and not limitation, the probe can be utilized to obtain ultrasound information taken at two diverse frequencies, such as 20 MHz and 40 MHz. It will be appreciated that any suitable frequency and any suitable quantity of frequencies may be used.

Generally, lower frequency information facilitates a tissue versus blood classification scheme due to the strong frequency dependence of the backscatter coefficient of the blood. Higher frequency information generally provides better resolution at the expense of poor differentiation between blood speckle and tissue, which can make it difficult to identify the lumen border. Thus, if information is obtained at a lower frequency and a higher frequency, then an algorithm can be utilized to interleave and display the two data sets to obtain frequency-diverse information that is closely aligned in time and space. In result, a high resolution ultrasound image can be produced with clear differentiation between blood and tissue and accurate delineation of vessel borders.

The typical 512 A-lines that compose a single frame of an image can be interspersed into alternating high and low frequency A-lines. As an example, a 20 MHz image can show the blood as black and the tissue as gray, while the 40 MHz image can show the blood and tissue as gray and barely, if at all, distinguishable from one another. It can be recognized through a provided algorithm that black in 20 MHz and gray at 40 MHz is blood, gray at both frequencies is tissue, and black at both frequencies is clear fluid. The broadband capability of advanced transducer technologies, such as PMUT, facilitated by the active spinning element, can allow for closely interleaved A-lines of two or more different center frequencies, possibly including pulse-inversion A-line pairs to generate harmonic as well as fundamental information, which is then combined to provide a robust classification scheme for tissue versus blood.

The dual frequency blood classification scheme can be further enhanced by other blood speckle reduction algorithms such as motion algorithms (such as ChromaFlo, Q-Flow, etc.), temporal algorithms, harmonic signal processing, etc. It will be appreciated that any suitable algorithm can be used.

Besides intravascular ultrasound, other types of ultrasound catheters can be made using the teachings provided herein. By way of example and not limitation, other suitable types of catheters include non-intravascular intraluminal ultrasound catheters, intracardiac echo catheters, laparoscopic, and interstitial catheters. In addition, the probe may be used in any suitable anatomy, including, but not limited to, coronary, carotid, neuro, peripheral, or venous.

Recitation of ranges of values herein are merely intended to serve as a shorthand method of referring individually to each separate value falling within the range, unless otherwise indicated herein, and each separate value is incorporated into the specification as if it were individually recited herein.

It will be appreciated that like reference numbers and/or like shown features in the figures can represent like features. It will be appreciated that discussions of like reference numbers and/or like shown features in any embodiment may be applicable to any other embodiment.

Any references, including publications, patent applications, and patents, cited herein are hereby incorporated by reference to the same extent as if each reference were individually and specifically indicated to be incorporated by reference and were set forth in its entirety herein (including any references contained therein).

Illustrative embodiments of a rotational IVUS probe incorporating an advanced ultrasound transducer technology are described herein. Variations of the disclosed embodiments will be apparent to those of ordinary skill in the art in view of the foregoing illustrative examples. Those skilled in the relevant art will employ such variations as appropriate, and such variations, embodied in alternative embodiments, are contemplated within the scope of the disclosed invention. The invention is therefore not intended to be limited to the examples described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A rotational intravascular ultrasound probe for insertion into a vasculature, the probe comprising:
   an elongate catheter having a flexible body, an elongate transducer shaft disposed within the flexible body, the transducer shaft having a drive cable and a transducer coupled to the drive cable adjacent a distal portion of the flexible body, and a proximal connector adjacent a proximal portion of the flexible body; and
   an interface module configured to interface with the proximal connector of the elongate catheter, the interface module including:
      a spinning element configured to be fixedly coupled to a proximal portion of the transducer shaft, the spinning element having an electronic component coupled thereto such that when the spinning element is fixedly coupled to the proximal portion of the transducer shaft the electronic component is in electrical contact with the transducer;
      a stationary element positioned adjacent to and spaced from the spinning element, wherein the stationary element is configured to pass signals to the spinning element and receive signals from the spinning element; and
      a motor coupled to the spinning element for rotating the spinning element and the transducer shaft when the spinning element is fixedly coupled to the proximal portion of the transducer shaft.

2. The rotational intravascular ultrasound probe of claim 1 wherein the spinning element has a printed circuit board, and the electronic component is attached to the printed circuit board.

3. The rotational intravascular ultrasound probe of claim 1 wherein the transducer is a PMUT transducer.

4. The rotational intravascular ultrasound probe of claim 1 wherein the transducer is a CMUT transducer.

5. The rotational intravascular ultrasound probe of claim 1 wherein the spinning element includes a generator for generating power for the transducer.

6. The rotational intravascular ultrasound probe of claim 1 wherein the electronic component is selected from the group consisting of a transmitter, a time-gain-control amplifier, an amplitude detector, a phase detector, an analog to digital converter, an optical transceiver, an encoder circuit, a wireless communication component, and a microcontroller.

7. The rotational intravascular ultrasound probe of claim 1 further comprising a printed circuit board having an algorithm stored thereon for interleaving data obtained at different frequencies from the transducer.

8. The rotational intravascular ultrasound probe of claim 1 further comprising at least three conductive lines electrically connecting the spinning element to the transducer.

9. An interface module for a rotational intravascular ultrasound probe for insertion into a vasculature, the interface module comprising:
   a connector for attachment to a proximal portion of a catheter having a transducer shaft with a transducer, the connector configured to fixedly engage with the transducer shaft such that the connector is in electrical communication with the transducer;
   a spinning element fixedly coupled to the connector, the spinning element having an electronic component coupled thereto that is in electrical contact with the connector such that when the connector is fixedly engaged with the transducer shaft the electronic component is in electrical communication with the transducer;
   a stationary element positioned adjacent to and spaced from the spinning element, wherein the stationary element is configured to pass signals to the spinning element and receive signals from the spinning element;
   a motor coupled to the spinning element for rotating the spinning element and the connector such that, when the connector is fixedly engaged with the transducer shaft, the transducer shaft rotates with the spinning element and the connector; and
   a housing, wherein at least the spinning element, stationary element, and motor are positioned within the housing.

10. The interface module of claim 9 wherein the spinning element has a printed circuit board, and the electronic component is attached to the printed circuit board.

11. The interface module of claim 9 wherein the spinning element is attached to an optical coupler.

12. The interface module of claim 9 wherein the spinning element includes a slip ring contact for a brush.

13. The interface module of claim 9 wherein the spinning element includes a generator for generating power for the transducer.

14. The interface module of claim 9 wherein the electronic component is selected from the group consisting of a transmitter, a time-gain-control amplifier, an amplitude detector a phase detector, an analog to digital converter, an optical transceiver, an encoder circuit, a wireless communication component, and a microcontroller.

15. The interface module of claim 9 further comprising a printed circuit board having an algorithm stored thereon for interleaving data obtained at different frequencies from the transducer.

16. The interface module of claim 9 wherein the connector includes at least three conductive lines electrically connected to the spinning element.

17. An interface module for a rotational intravascular ultrasound probe for insertion into a vasculature, the interface module comprising:
   a housing;
   a printed circuit board positioned within the housing;
   a connector for attachment to a proximal portion of a catheter having a transducer shaft with a transducer, the connector configured to fixedly engage with the transducer shaft such that the connector is in electrical communication with the transducer;
   a spinning element fixedly coupled to the connector, the spinning element having more than two signal pathways electrically connecting the spinning element to the connector such that when the connector is fixedly engaged with the transducer shaft at least one of the two signal pathways electrically connects the spinning element to the transducer;
   a stationary element positioned within the housing adjacent to and spaced from the spinning element, wherein the stationary element is configured to pass signals to the spinning element and receive signals from the spinning element, the stationary element electrically coupled to the printed circuit board; and
   a motor positioned within the housing and coupled to the spinning element for rotating the spinning element and the connector such that, when the connector is fixedly engaged with the transducer shaft, the transducer shaft rotates with the spinning element and the connector.

18. The interface module of claim 17 wherein the spinning element includes at least one of a rotary transformer, a slip ring contact for a brush, a power generator, a wireless communication component, and an optical communication component.

19. A rotational intravascular ultrasound device, the device comprising:
- an elongate catheter having a flexible body, an elongate transducer shaft disposed within the flexible body, and at least one transducer coupled to the transducer shaft adjacent a distal portion of the flexible body;
- a connector fixedly secured to a proximal portion of the transducer shaft such that the connector is in electrical communication with the at least one transducer;
- a spinning element fixedly coupled to the connector, the spinning element having planar flex circuit coupled thereto, wherein the spinning element is in electrical contact with the connector such that when the connector is fixedly secured to the proximal portion of the transducer shaft the planar flex circuit is in electrical communication with the at least one transducer; and
- a stationary element positioned adjacent to and spaced from the spinning element, the stationary element including a planar flex circuit configured to pass signals to the planar flex circuit of the spinning element and receive signals from the planar flex circuit of the spinning element.

20. The rotational ultrasound device of claim 19, further comprising a housing, wherein at least the spinning element and the stationary element are positioned within the housing.

* * * * *